US008617403B1

(12) United States Patent
Peters et al.

(10) Patent No.: US 8,617,403 B1
(45) Date of Patent: Dec. 31, 2013

(54) METHODS AND STABILIZED COMPOSITIONS FOR REDUCING DEPOSITS IN WATER SYSTEMS

(71) Applicant: Blue Earth Labs, LLC, Las Vegas, NV (US)

(72) Inventors: Jason E. Peters, Shawnee, KS (US); Stephen D. O'Connor, Leawood, KS (US); Chang-jun Yu, Pasadena, CA (US)

(73) Assignee: Blue Earth Labs, LLC, Las Vegas, NV (US)

( * ) Notice: Subject to any disclaimer, the term of this patent is extended or adjusted under 35 U.S.C. 154(b) by 0 days.

(21) Appl. No.: 13/950,147

(22) Filed: Jul. 24, 2013

Related U.S. Application Data

(60) Provisional application No. 61/839,324, filed on Jun. 25, 2013.

(51) Int. Cl.
*C02F 1/76* (2006.01)

(52) U.S. Cl.
USPC ........ 210/748.2; 210/756; 210/758; 210/192; 252/186.21; 205/556

(58) Field of Classification Search
USPC ......... 210/743, 746, 748.2, 748.17, 749, 753, 210/756, 758, 764, 192; 252/186.1, 252/187.1–187.32; 205/556
See application file for complete search history.

(56) References Cited

U.S. PATENT DOCUMENTS

| | | | |
|---|---|---|---|
| 4,139,449 A | 2/1979 | Goto et al. | |
| 4,240,884 A | 12/1980 | Pellegri | |
| 4,308,117 A | 12/1981 | Sweeney | |
| 4,329,215 A | 5/1982 | Scoville | |
| 4,411,759 A | 10/1983 | Olivier | |
| 4,545,863 A | 10/1985 | Yeager et al. | |
| 4,585,539 A | 4/1986 | Edson | |
| 4,686,018 A | 8/1987 | Chaussard | |
| 4,693,806 A | 9/1987 | Tucker | |
| 4,761,208 A | 8/1988 | Gram et al. | |
| 4,767,511 A | 8/1988 | Aragon | |

(Continued)

FOREIGN PATENT DOCUMENTS

| CA | 1 263 095 A1 | 11/1989 |
|---|---|---|
| EP | 0201951 B1 | 5/1990 |

(Continued)

OTHER PUBLICATIONS

Response to Office Action filed Nov. 17, 2004 in U.S. Trademark Application No. 78/325,434 (RE-Ox) with specimen label, identifying date of first use as Nov. 2003.

(Continued)

*Primary Examiner* — Lucas Stelling
(74) *Attorney, Agent, or Firm* — Vincent K. Gustafson; Jenkins, Wilson, Taylor & Hunt, P.A.

(57) ABSTRACT

A stabilized mixed oxidant solution may be produced by flowing a starting solution (e.g., salt brine, hypochlorous acid, and/or sodium hypochlorite) through a flow-through electrochemical module including first and second passages separated by an ion permeable membrane while electric power is applied between an anode and cathode in electrical communication with the first and second passages, respectively. An initially acidic anolyte solution received from the first (anode) passage is stabilized by elevating pH to yield a stabilized mixed oxidant solution. Methods of using the mixed oxidant solution are further provided.

29 Claims, 8 Drawing Sheets

(56) References Cited

U.S. PATENT DOCUMENTS

| | | | |
|---|---|---|---|
| 4,786,380 | A | 11/1988 | van Duin et al. |
| 5,037,519 | A | 8/1991 | Wiscombe |
| 5,082,543 | A | 1/1992 | Gnann et al. |
| 5,124,017 | A | 6/1992 | Rogov et al. |
| 5,314,629 | A | 5/1994 | Griese et al. |
| 5,405,507 | A | 4/1995 | Bishara et al. |
| 5,427,667 | A | 6/1995 | Bakhir et al. |
| 5,624,544 | A | 4/1997 | Deguchi et al. |
| 5,628,888 | A | 5/1997 | Bakhir et al. |
| 5,635,040 | A | 6/1997 | Bakhir et al. |
| 5,693,212 | A | 12/1997 | Mazanec et al. |
| 5,783,052 | A | 7/1998 | Bakhir et al. |
| 5,858,201 | A | 1/1999 | Otsuka et al. |
| 5,871,623 | A | 2/1999 | Bakhir et al. |
| 5,932,171 | A | 8/1999 | Malchesky |
| 5,938,916 | A | 8/1999 | Bryson et al. |
| 5,958,229 | A | 9/1999 | Filiopoulos et al. |
| 6,033,539 | A | 3/2000 | Gablenko |
| 6,059,941 | A | 5/2000 | Bryson et al. |
| 6,063,247 | A | 5/2000 | Bergmann et al. |
| 6,217,741 | B1 | 4/2001 | Doi |
| 6,296,744 | B1 | 10/2001 | Djeiranishvili et al. |
| 6,528,214 | B1 | 3/2003 | Pliner et al. |
| 6,558,537 | B1 | 5/2003 | Herrington et al. |
| 6,623,695 | B2 | 9/2003 | Malchesky et al. |
| 6,632,347 | B1 | 10/2003 | Buckley et al. |
| 6,752,757 | B2 | 6/2004 | Muir et al. |
| 6,805,787 | B2 | 10/2004 | Bess et al. |
| 6,811,710 | B2 | 11/2004 | Simmons |
| 6,843,895 | B2 | 1/2005 | Bakir et al. |
| 6,860,976 | B2 | 3/2005 | Andrews et al. |
| 7,090,753 | B2 | 8/2006 | Sumita |
| 7,276,255 | B2 | 10/2007 | Selkon |
| 7,303,660 | B2 | 12/2007 | Buckley et al. |
| 7,374,645 | B2 | 5/2008 | Davis et al. |
| 7,691,249 | B2 | 4/2010 | Daly et al. |
| 8,002,955 | B2 | 8/2011 | Daly et al. |
| 8,062,500 | B2 | 11/2011 | Sumita |
| 8,366,939 | B2 | 2/2013 | Vineyard et al. |
| 8,518,270 | B1 | 8/2013 | Vineyard et al. |
| 2001/0022273 | A1 | 9/2001 | Popov et al. |
| 2002/0182262 | A1 | 12/2002 | Selkon |
| 2003/0133878 | A1 | 7/2003 | Hinze |
| 2004/0055896 | A1 | 3/2004 | Anderson et al. |
| 2005/0029093 | A1 | 2/2005 | Rawhani et al. |
| 2005/0121334 | A1 | 6/2005 | Sumita |
| 2006/0049118 | A1 | 3/2006 | Robles |
| 2006/0124453 | A1 | 6/2006 | Cross |
| 2006/0249375 | A1 | 11/2006 | Aoun et al. |
| 2006/0278585 | A1 | 12/2006 | Cocking |
| 2007/0017820 | A1 | 1/2007 | Anderson et al. |
| 2007/0051640 | A1 | 3/2007 | Bellamy |
| 2007/0108064 | A1 | 5/2007 | Buckley et al. |
| 2008/0116144 | A1 | 5/2008 | Vineyard et al. |
| 2011/0100927 | A1 | 5/2011 | Vineyard et al. |
| 2013/0146471 | A1 | 6/2013 | Dubois et al. |
| 2013/0146472 | A1 | 6/2013 | Sullivan et al. |
| 2013/0146473 | A1 | 6/2013 | Lambert et al. |
| 2013/0146474 | A1 | 6/2013 | Sullivan et al. |

FOREIGN PATENT DOCUMENTS

| | | |
|---|---|---|
| JP | 01-104387 A | 4/1989 |
| WO | WO-2007-057940 A1 | 5/2007 |
| WO | WO 2011/142671 A1 | 11/2011 |
| WO | WO 2013/090560 A2 | 6/2013 |

OTHER PUBLICATIONS

Dreeszen, P. "The key to understanding and controlling bacterial growth in Automated Drinking Water Systems, Second Ed." Jun. 2003, Edstrom Industries, Inc.

Dandoy et al. "Disinfection of Water systems" 1978, Arizona Division of Environmental Health Services, Bureau of Water Quality Control.

"Lectranator II: Commercial Operation / Installation Manual" Lectranator Systems, Inc., 2003.

Bergsrud et al. "Treatment Systems for Household Water Supplies: Chlorination," 1992, North Dakota State University.

"AWS Technical Report: Sanitizing Pipelines & Distribution Systems by Shock-Chlorination," 2003, AWS, Inc.

Bard, et al. "Electrochemical Methods: Fundamentals and Applications" 1980, John Wiley & Sons, Inc. pp. 14-16.

Pisarenko et al, New Development in Sodium Hypochlorite Manufacturing—High Strength Low Salt Bleach (2013).

Hill Brothers, "Product Profile—Sodium Hypochlorite NaOCl" Chemical Company (Orange, California), Nov. 2011.

Emerson Process Management, "Fundamentals of ORP Measurement" Application Data Sheet, Rosemount Analytical, Inc., Irvine, California, May 2008.

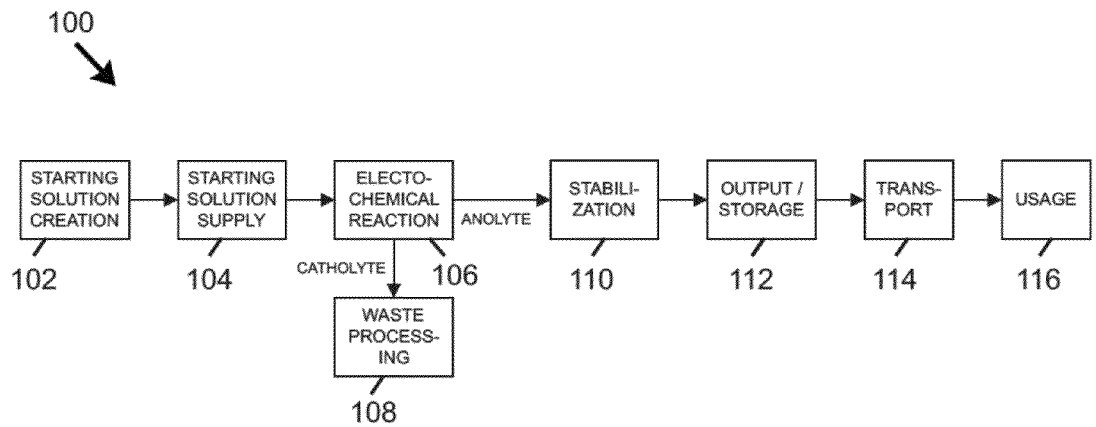
FIG._1
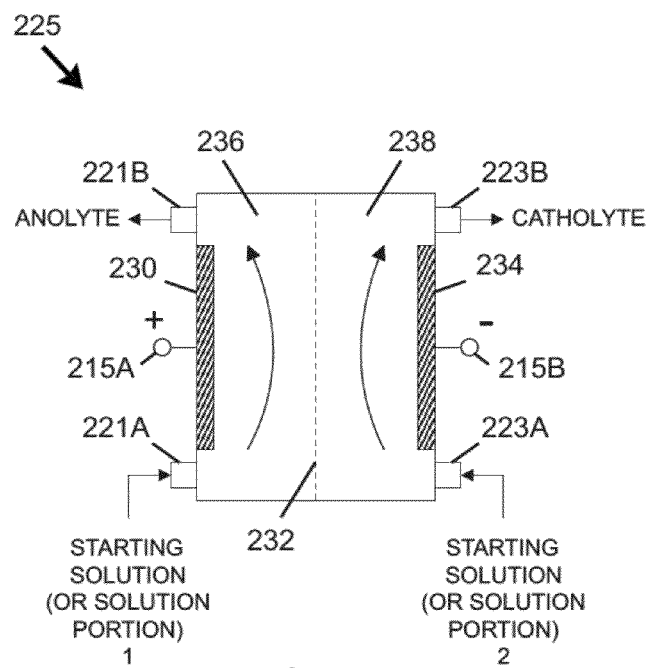
FIG._2

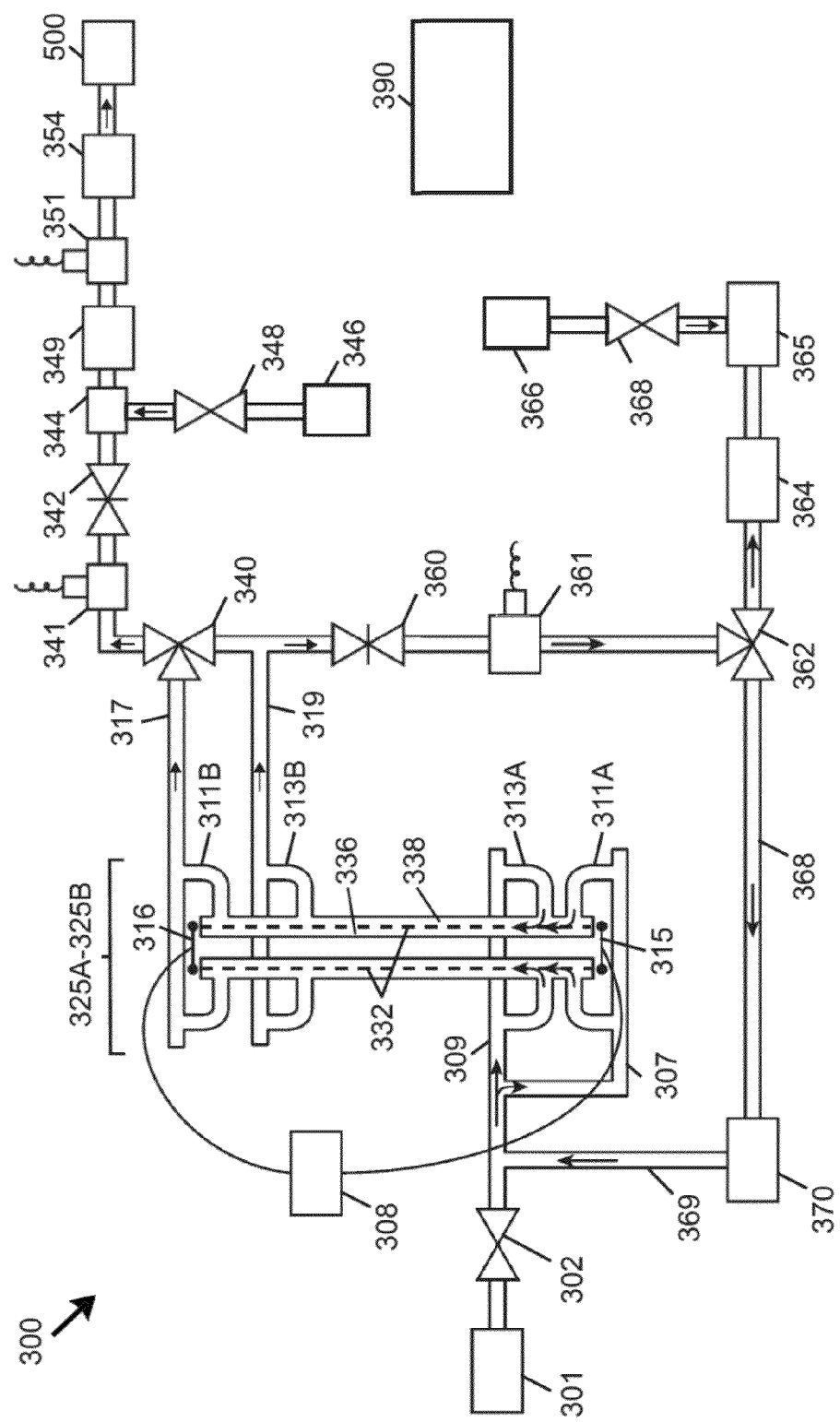
FIG._3

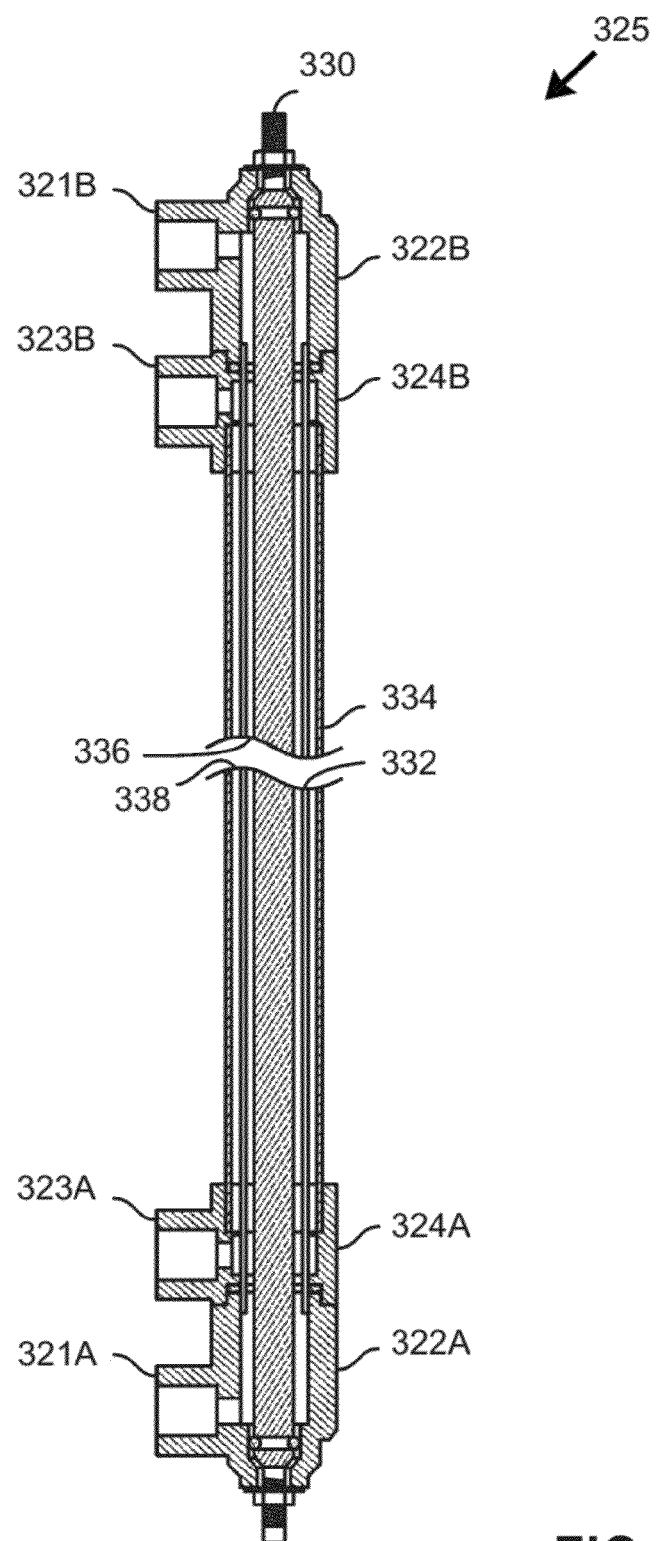
FIG._4

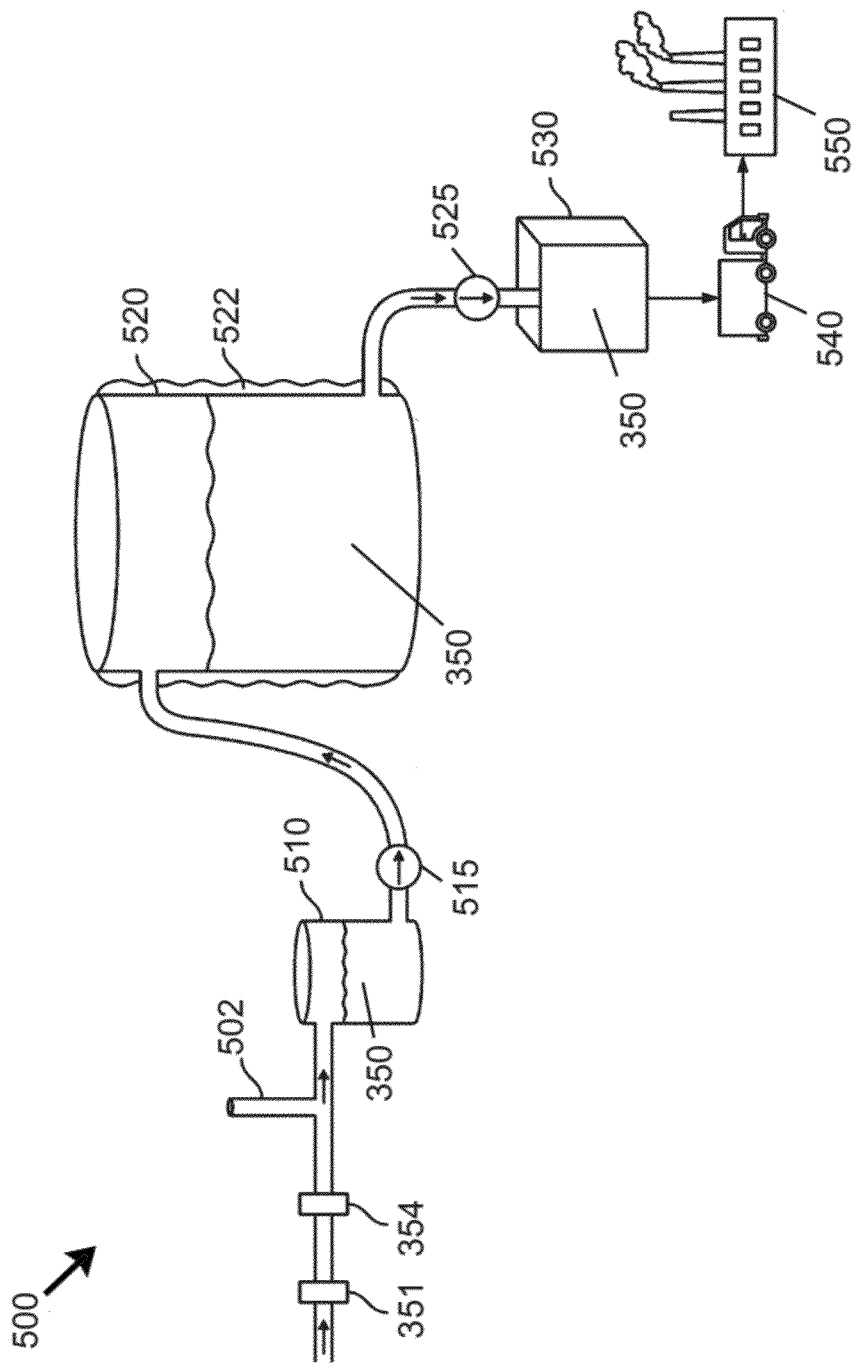
FIG._5

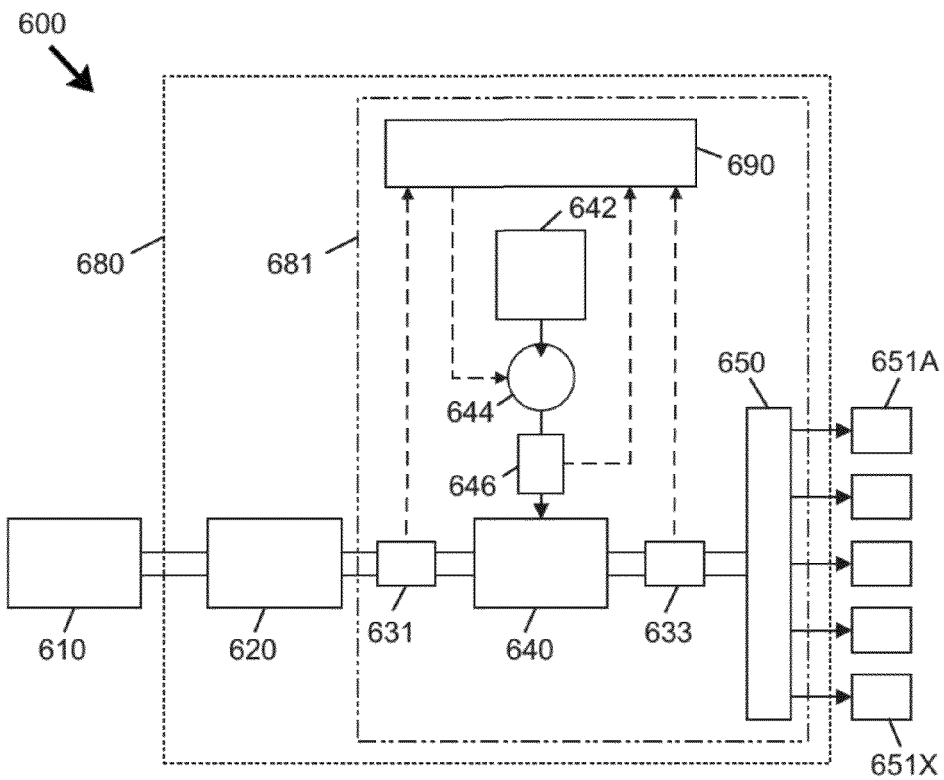
FIG._6
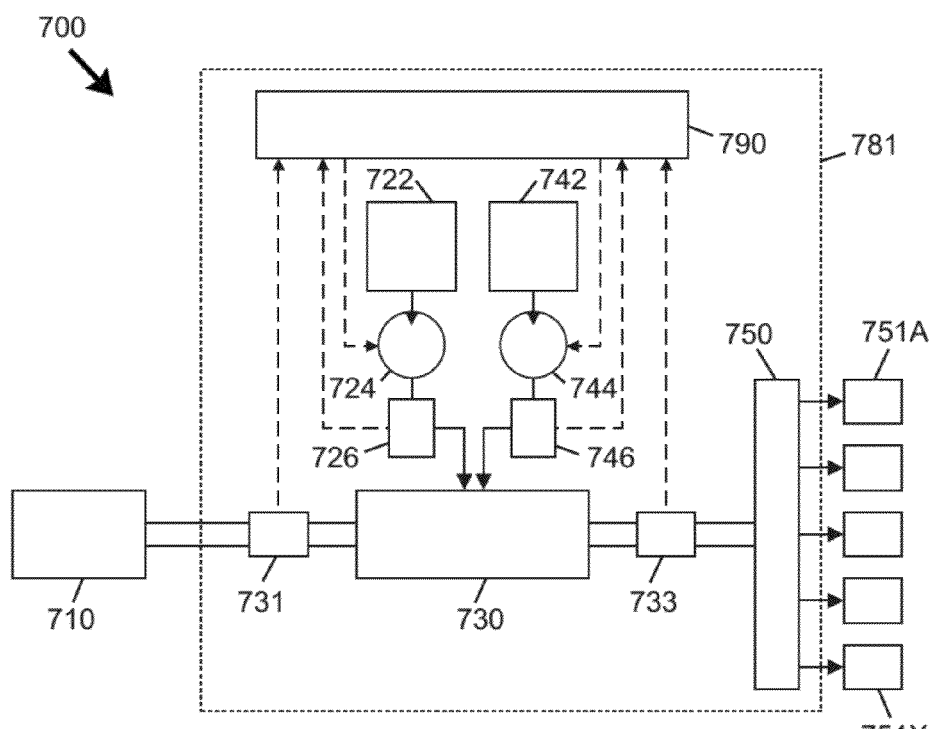
FIG._7

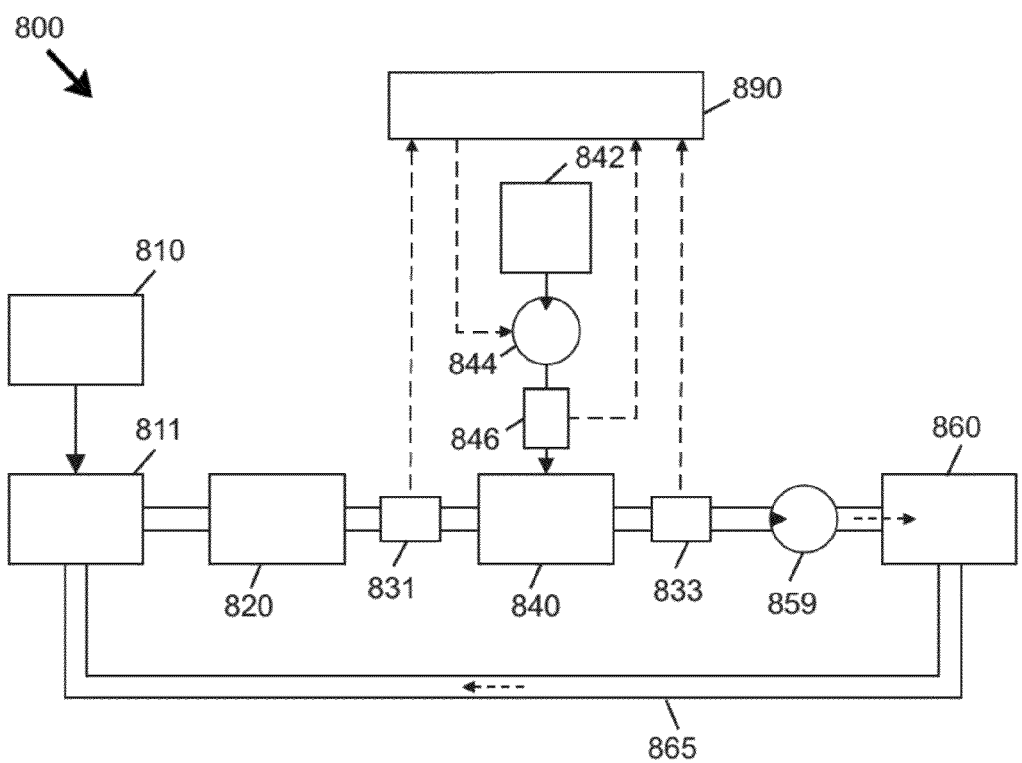
FIG._8

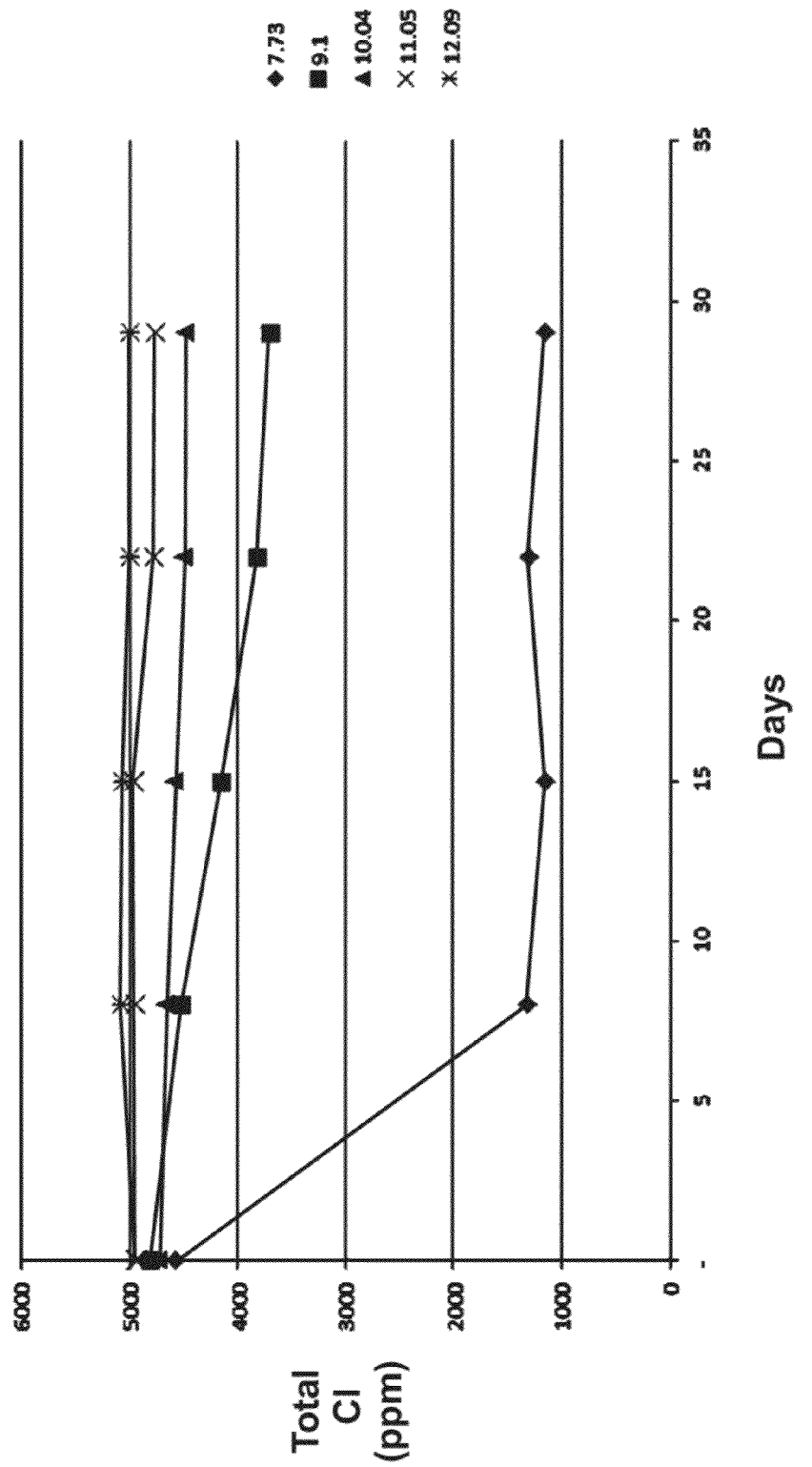
FIG._9

| Product | Total Cl (ppm) | pH | ORP (mV) | Cond. (mS/cm) | Na+ (g/L) * | Cl- (g/L) ** | Ratio Na+/Cl- |
|---|---|---|---|---|---|---|---|
| Bleach 1 (12.5%) | 149440 | 12.96 | 576.6 | 131.0 *** | | | |
| Dup. | 135040 | 12.09 | 562.5 | 131.9 *** | | | |
| Avg. | 142240 | 12.53 | 569.6 | **131.5 *** ** | 93.60 | 94.30 | 0.99 |
| Bleach 2 (6%) | 58240 | 12.39 | 596.0 | 112.1 | | | |
| Dup. | 58240 | | 582.1 | 110.4 | | | |
| Avg. | 58240 | 12.39 | 589.1 | 111.25 | 36.50 | 39.70 | 0.92 |
| Clearitas mixed oxidant | 590 | 6.65 | 902.3 | 7.86 | | | |
| Dup. | 610 | 6.72 | 937.3 | 7.86 | | | |
| Avg. | 600 | 6.69 | 919.8 | 7.86 | 2.56 | 1.59 | 1.61 |
| Miox" mixed oxidant (2 mo old in Ref.) | 3740 | 9.10 | 811.9 | 61.7 | | | |
| Dup. | 3820 | 9.14 | 822.0 | 61.8 | | | |
| Avg. | 3780 | 9.12 | 817.0 | 61.75 | 23.00 | 15.70 | 1.46 |
| New stabilized mixed oxidant | 1600 | 10.45 | 676.1 | 17.44 | | | |
| Dup. | 1500 | 10.47 | 690.6 | 17.33 | | | |
| Avg. | 1550 | 10.46 | 683.4 | 17.385 | 5.87 | 3.87 | 1.52 |

\* Method EPA 300.00
\*\* Method EPA 6010
\*\*\* diluted (at 2x dilution)

FIG. 10

METHODS AND STABILIZED COMPOSITIONS FOR REDUCING DEPOSITS IN WATER SYSTEMS

STATEMENT OF RELATED APPLICATION(S)

This application claims priority to U.S. Provisional Patent Application No. 61/839,324 filed on Jun. 25, 2013, which application is hereby incorporated by reference herein in its entirety.

BACKGROUND

Water commonly contains organic matter, dissolved solids, and minerals that deposit scale and film (e.g., biofilm) on surfaces in drinking water distribution pipes and equipment. Quality and flow of drinking water may be deleteriously affected by such scales and films. Various cleaning and sanitizing agents may additionally leave film residues. Use of methods and compositions described herein may usefully reduce, remove, or prevent formation of these deposits.

Chlorine and chlorine-based disinfectants (including sodium hypochlorite, also known as liquid bleach) are used worldwide to reduce pathogens in drinking water. Chlorine and chlorine-based disinfectants have been widely adopted because they provide a "residual" level of protection against waterborne pathogens—namely, a low level of chlorine remaining in water after initial disinfectant application, which reduces the risk of subsequent microbial contamination after treatment. Upon initial dosing, chlorine reacts with any organic matter in water, with the amount of chlorine used in such reactions being known as the "chlorine demand" of the water. Some portion of the remaining chlorine reacts with nitrogen in water to form chloramines (with the chlorine consumed by such reactions being known as "combined chlorine"). Chloramines may also be intentionally added to water systems. Chlorine remaining in the water after chlorine demand is satisfied and combined chlorine is formed is termed "free chlorine," which is the chlorine portion available for disinfection (e.g., to kill or incapacitate reproduction of waterborne pathogens). Chlorine residual is typically monitored at various points in drinking water distribution systems to identify points at which the residual declines or disappears—which may indicate a leak in the water distribution system or growth of bacteria.

A variable matrix of organic and inorganic deposits (variously referred to as biofilms, scale, or tuberculations) accumulates on the interior surfaces of all drinking water distribution piping systems. Control of such deposits provides advantages including improved water quality, reduced maintenance costs, and efficient use of disinfectants. Organic-laden deposits are a significant source of increased chlorine demand and can produce precursors of trihalomethanes and haloacetic acids or other disinfection byproducts. Such organic-laden deposits in drinking water systems have been shown to harbor and protect pathogenic or otherwise troublesome bacteria, viruses, algae, algal toxins, fungi, protozoa, and invertebrates. Many types of microorganisms can proliferate in these organic-laden deposits, and toxic by-products of such microorganisms can become problematic. Regardless of the level of residual disinfectant, microorganisms harbored in organic-laden deposits have been demonstrated to periodically slough off and re-entrain into flowing water, thereby contaminating other systems and exposing susceptible water consumers to biological hazards from drinking water systems (e.g., in buildings occupied by such consumers).

Many consumers are familiar with inorganic "scale" such as occurs in a teapot following the boiling of hard water. The familiar white precipitate is predominantly calcium carbonate, which deposits onto wetted surfaces of the teapot because the solubility of the salt is inversely related to temperature: as the temperature increases, the salt precipitates. In drinking water systems, however, the scaling process is more complex and the water is not boiled (it is noted that boiling water has a very destructive effect on organic compounds in water). Deposits in drinking water systems typically are not limited to just calcium carbonate or other inorganic substances, since organic materials in the water are prone to adhering to surfaces. Native organic compounds from bulk drinking water accumulate onto surfaces because adsorption is thermodynamically favored. Consequently, the deposits on surfaces in drinking water distribution systems include organic compounds in combination with inorganic compounds. The presence of organic materials give surface deposits in drinking water systems characteristics that are substantially different from inorganic scale deposits (e.g., such as may be observed on a wetted surface of a tea pot).

Primary disinfectants such as chlorine gas and liquid bleach have very limited ability to control deposits composed of both organic and inorganic constituents in drinking water systems. To the contrary, high concentration of liquid bleach in water distribution systems are typically avoided, since high concentrations have been observed to contribute to scale formation in pipes.

In order to reduce accumulation of deposits on surfaces in water distribution systems, liquid compositions including mixed oxidants or supplemental oxidants (also termed "activated sodium hypochlorite") such as RE-Ox® scale control additive have been developed. As disclosed in U.S. Pat. No. 8,366,939 (which is commonly assigned to the same assignee of the present application, and is hereby incorporated by reference herein), liquid including supplemental oxidants may be produced by flowing salt brine solution through at least one flow electrode module comprising a center anode, a membrane surrounding the center anode, and an outer cathode surrounding the membrane, wherein at least a portion of the solution is flowed serially through an outside passage disposed between the membrane and the outer cathode, and then through an inside passage disposed between the center anode and the membrane, while electric power is applied between the anode and the cathode to electrolyze said solution, to produce a liquid desirably having a pH in a range of from about 5 to about 7.5 (with such patent also describing the product as having a "neutral pH"). The resulting composition may be supplied to water distribution systems at low concentration (e.g., from 1 to 100 ppb) to promote scale control, reduce chlorine demand, and reduce disinfection by-products.

U.S. Pat. No. 8,366,939 recognizes that a large concern in supplying activated sodium hypochlorite is shelf life, noting that degradation is caused as chlorine gas is off gassed, thereby lowering pH and lowering chlorine content. As a result, some producers of liquid compositions including supplemental oxidants have reported a shelf life of only 2 weeks, whereas the process described in U.S. Pat. No. 8,366,939 may yield a somewhat greater effective shelf life of 3 months or more. In recognition of the comparatively short shelf life of mixed oxidant solutions, certain manufacturers produce systems for on-site generation of mixed oxidants by electrolysis of a brine solution produced from water and salt.

It would be desirable to provide scale control and water treatment compositions suitable for water distribution systems with enhanced effectiveness (to provide advantages such as reduced shipping weight, reduced storage volume, and reduced size and cost of dosing equipment such as pumps and valves) in combination with extended effective shelf life; however, it is understood that increased concentration of chlorine species tends to result in faster decomposition rate (and faster loss of concentration of active ingredient), thereby inhibiting the ability to satisfy the foregoing criteria simultaneously.

Various compositions and methods disclosed herein address limitations associated with conventional compositions and methods.

SUMMARY

Various aspects of the invention relate to production and use of mixed oxidant solutions exhibiting enhanced effectiveness and enhanced stability compared to prior solutions, with the resulting mixed oxidant solutions being particularly useful for water treatment (e.g., for primary disinfection or secondary disinfection) and/or reducing deposits in water distribution or water recirculation systems.

In one aspect, the invention relates to a method for producing a mixed oxidant solution comprising a plurality of different oxidants from a starting solution comprising at least one of salt brine, hypochlorous acid, and sodium hypochlorite, the method comprising: flowing at least one starting solution through at least one flow-through electrochemical module comprising a first passage and a second passage separated by an ion permeable membrane while electric power is applied between (i) an anode in electrical communication with the first passage and (ii) a cathode in electrical communication with the second passage, wherein a first solution or first portion of the at least one starting solution is flowed through the first passage to form an anolyte solution having an acidic pH, and a second solution or second portion of the at least one starting solution is simultaneously flowed through the second passage to form a catholyte solution having a basic pH; and contacting the anolyte solution with a hydroxide solution to attain a pH value of at least about 9.0 (or another desired pH value such as preferably at least about 10.0, preferably at least about 11.0, preferably at least about 12.0, or preferably at least about 13.0) to yield said mixed oxidant solution. In certain embodiments, the mixed oxidant solution may be packaged in at least one container and transported to a treatment facility associated with a water distribution system or water recirculation system.

In another aspect, the invention relates to a mixed oxidant solution produced by a method including the steps of the foregoing production method.

In another aspect, the invention relates to a method for promoting disinfection and reduction of deposits in a water distribution or water recirculation system, the method comprising supplying to the water distribution or water recirculation system an effective amount of the mixed oxidant solution (comprising a plurality of different oxidants) produced by a method including the steps of the foregoing production method. In certain embodiments, the supplying of mixed oxidant solution to the water distribution or recirculation system is sufficient to elevate oxidant concentration in the water distribution or water recirculation system by 0.2 ppm to 0.6 ppm relative to water present in the water distribution or water recirculation system prior to the step of supplying mixed oxidant solution. In certain embodiments, the supplying of mixed oxidant solution to the water distribution or recirculation system is sufficient to elevate oxidant concentration in the water distribution or water recirculation system by 1 ppb to 100 ppb relative to water present in the water distribution or water recirculation system prior to the step of supplying mixed oxidant solution.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Other aspects, features and embodiments of the invention will be more fully apparent from the ensuing disclosure and appended claims.

BRIEF DESCRIPTION OF THE DRAWINGS

FIG. 1 is a flow chart showing various stages involved in making and/or using a mixed oxidant solution according to the present invention.

FIG. 2 is a simplified schematic cross-sectional view of a flow-through electrochemical module including flow chambers separated by an ion-permeable membrane and arranged to produce separate anolyte and catholyte streams by electrolysis of a salt brine solution.

FIG. 3 is a schematic diagram showing arrangement of a mixed oxidant solution production system including flow-through electrochemical modules and associated components.

FIG. 4 is a cross-sectional view of an exemplary flow-through electrochemical module.

FIG. 5 is a schematic diagram showing components of an output subsystem to receive an output stream from the mixed oxidant solution production system of FIG. 3.

FIG. 6 is a schematic diagram showing components of a first water distribution system arranged to receive a mixed oxidant solution according to the present invention.

FIG. 7 is a schematic diagram showing components of a second water distribution system arranged to receive a mixed oxidant solution according to the present invention.

FIG. 8 is a schematic diagram showing components of a water recirculation system arranged to receive a mixed oxidant solution according to the present invention.

FIG. 9 is a line chart depicting total chlorine (ppm) versus time (days) for mixed oxidant solutions produced using the system of FIG. 3.

FIG. 10 is a table summarizing characteristics including total chlorine, pH, oxidation-reduction potential, conductivity, sodium ion concentration, chloride ion concentration, and sodium/chloride ion ratio for the following five products: (1) 12.5% hypochlorite bleach, (2) 6% hypochlorite bleach, (3) Clearitas® mixed oxidant solution, (4) Miox™ mixed oxidant solution, and (5) a (new) stabilized mixed oxidant solution according to the present invention.

DETAILED DESCRIPTION

Described herein are methods for making and using novel mixed oxidant solutions that exhibit enhanced effectiveness and enhanced stability compared to prior solutions, with the novel mixed oxidant solutions being particularly useful for water treatment and/or reducing deposits in water distribution and/or water recirculation systems. In contrast to prior solutions (e.g., RE-Ox® chemical solution described in U.S. Pat. No. 8,366,939 and Clearitas® mixed oxidant solution commercialized by Blue Earth Labs, LLC of Las Vegas, Nev., US) resulting from electrolyzing a brine solution in a flow-through cathode chamber followed by electrolysis of the catholyte solution in a flow-through anode chamber, various novel mixed oxidant solutions described herein beneficially contain anolyte solution produced by flowing at least one starting solution (i.e., comprising at least one of salt brine, hypochlorous acid, and sodium hypochlorite) through an anode chamber without prior or subsequent transmission through a cathode chamber, wherein the resulting anolyte solution is immediately treated with a hydroxide solution to attain a mixed oxidant solution having a basic pH—preferably with a pH value of at least about 9.0, at least about 9.5, at least about 10.0, at least about 10.5, at least about 11.0, at least about 11.5, at least about 12.0, at least about 12.5, or at least about 13.0—to yield the mixed oxidant solution. Elevated pH of the resulting mixed oxidant solution has been found to significantly increase the effective shelf life of the solution, even in the presence of high concentrations of mixed oxidants. The stabilized mixed oxidant solution can be centrally produced, packaged, and delivered to a customer without necessity for the solution to be manufactured at the point of use.

Certain embodiments are directed to a method for producing a mixed oxidant solution comprising a plurality of different oxidants from a starting solution comprising at least one of salt brine, hypochlorous acid, and sodium hypochlorite, the method comprising: flowing at least one starting solution through at least one flow-through electrochemical module comprising a first passage and a second passage separated by an ion permeable membrane while electric power is applied between (i) an anode in electrical communication with the first passage and (ii) a cathode in electrical communication with the second passage, wherein a first solution or first portion of the at least one starting solution is flowed through the first passage to form an anolyte solution having an acidic pH, and a second solution or second portion of the at least one starting solution is simultaneously flowed through the second passage to form a catholyte solution having a basic pH; and contacting the anolyte solution with a hydroxide solution to attain a pH value of at least about 9.0 (or another desired pH value such as preferably at least about 10.0, preferably at least about 11.0, preferably at least about 12.0, or preferably at least about 13.0) to yield said mixed oxidant solution.

In certain embodiments, at least one starting solution comprises salt brine. In certain embodiments, at least one starting solution comprises at least one of hypochlorous acid and sodium hypochlorite.

In certain embodiments, catholyte solution produced by the at least one flow-through electrochemical module is discarded, preferably following partial or full neutralization by contacting the catholyte solution with an acid.

In certain embodiments, at least one flow-through electrochemical module includes a centrally-arranged anode, a membrane surrounding the anode, a cathode surrounding the membrane, a first passage comprising an inner passage arranged between the anode and the membrane, and a second passage comprising an outer passage arranged between the membrane and the cathode. Electrochemical modules having different geometries and conformations may be used.

In certain embodiments, a mixed oxidant solution may be packaged in at least one container, and the container(s) may be transported to a treatment facility associated with said water distribution or water recirculation system.

In certain embodiments, characteristics of the at least one starting solution, flow rate of the at least one starting solution, materials of construction of the at least one flow-through electrochemical module, dimensions of the at least one flow-through electrochemical module, number of the at least one flow-through electrochemical module, conformation of the at least one flow-through electrochemical module, and field density of the applied electric power are selected to yield a mixed oxidant solution having desired properties. Such properties may include one or more of the following: an oxidation-reduction potential (ORP) value in a range of from 500 mV to 900 mV (or in a range of from 600 mV to 900 mV, or in a range of from 600 mV to 800 mV); a ratio of Na+ (in g/L according to Method EPA 300.0) to Cl− (in g/L according to Method EPA 6010) of at least about 1.5; and total chlorine value of at least about 1000 ppm, at least about 3000 ppm, at least about 5000 ppm, in a range of from about 1,000 ppm to about 3,500 ppm, or in a range of from about 1,000 ppm to about 6,000 ppm. In certain embodiments, multiple values in the foregoing ranges for ORP, Na+:Cl−, and total Cl (e.g., one value for ORP, another value for Na+:Cl−, and/or another value for total Cl) may be present in the same mixed oxidant solution.

In certain embodiments, a method for promoting disinfection and reduction of deposits in a water distribution or water recirculation system, the method comprising supplying an effective amount of a stabilized mixed oxidant solution (i.e., produced according to methods disclosed herein) to the water distribution or water recirculation system.

In certain embodiments, a stabilized mixed oxidant solution may be provided in sufficient amount to provide primary disinfection and scale control utility. In certain embodiments, the supplying of mixed oxidant solution to the water distribution or recirculation system is sufficient to elevate oxidant concentration (i.e., total oxidant concentration, which may be approximated by measuring total chlorine) in the water distribution or water recirculation system by 0.2 ppm to 0.6 ppm relative to water present in the water distribution or water recirculation system prior to the step of supplying mixed oxidant solution. Such oxidant concentration values are sufficient to provide primary disinfection utility without requiring presence of any other primary disinfectant, such that water present in the water distribution or water recirculation system may be devoid of primary disinfectant prior to the step of supplying mixed oxidant solution.

In other embodiments, a stabilized mixed oxidant solution may be provided in sufficient amount to provide scale control utility and secondary disinfection utility. In certain embodiments, the supplying of mixed oxidant solution to the water distribution or recirculation system is sufficient to elevate oxidant concentration in the water distribution or water recirculation system by 1 ppb to 100 ppb (or by 1 ppb to 50 ppb) relative to water present in the water distribution or water recirculation system prior to the step of supplying mixed oxidant solution. Such oxidant concentration values are sufficient to provide scale control utility and secondary disinfection utility, but the water present in such system may optionally comprise a primary disinfectant prior to the step of supplying mixed oxidant solution. When stabilized mixed oxidant solutions are provided to a water distribution or water treatment system to yield a mixed oxidant concentration of from 1 to 100 ppb (or from 1 to 50 ppb), the resulting mixed oxidant concentration is very low—below concentrations that would have significant antimicrobial effect—but may still be effective in reducing chlorine demand, reducing disinfection by-products (e.g., THMs and HAA5s), and controlling deposits. At such levels in the parts per billion range, oxidants present in the stabilized mixed oxidant solutions are effective in oxidizing certain components of deposits (e.g., organic and inorganic compounds) in order to promote their removal.

In addition to the foregoing benefits, stabilized mixed oxidant solutions disclosed herein may also be useful to provide water softening utility—in some instance sufficient to eliminate need for ion exchange water softening.

Stabilized mixed oxidant solutions disclosed herein may be added to various water distribution, water recirculation, and/or water treatment systems. In certain embodiments, a water distribution or water recirculation system may comprise water lines within a building (including, but not limited to, a healthcare facility such as a hospital, a food or beverage processing facility, or an industrial facility). In certain embodiments, a water distribution system may comprise a municipal or community drinking water distribution system arranged to supply potable water to water utilizing facilities of a plurality of different customers. In certain embodiments, a water distribution system may comprise a drinking water distribution system for humans or animals. In certain embodiments, a water distribution system may comprise an agricultural water distribution system. In certain embodiments, a water distribution or water recirculation system may comprise an aquaculture system or hydroponic food production system. In certain embodiments, a water distribution or water recirculation system may comprise a cooling water system, such as may include one or more cooling towers or other heat exchange apparatuses. In certain embodiments, a water treatment or water recirculation system may comprise a wastewater system.

Novel mixed oxidant solutions described herein may be beneficially used to reduce formation of, and/or remove, scale and biofilm deposits from fluid conduits (e.g., pipes) and other wetted surfaces during normal operations while maintaining water quality. Such mixed oxidant solutions readily penetrate inorganic deposits as well as organic deposits/biofilms to break down and remove the organic 'glue' that holds such deposits and films together. Mixed oxidant solutions as described herein may be beneficially used in numerous water distribution and water circulation contexts—such as (but not limited to) human drinking water, animal drinking water, food processing, agriculture (including hydroponic food production), aquaculture (including fish or shellfish harvesting), industrial water (including cooling towers), and healthcare (e.g., hospitals and similar facilities). One noteworthy benefit of stabilized mixed oxidant solutions as described herein is the ability to eliminate persistent pathogens such as *Legionella* bacteria from water distribution systems.

As illustrated in FIG. 1, a system 100 for producing, transporting, and/or using a stabilized mixed oxidant solution may involve multiple stages, such as: starting solution creation 102, starting solution supply 104, electrochemical processing 106, waste processing 108 (e.g., as applied to a catholyte stream), stabilization 110 (e.g., as applied to an anolyte stream), output/storage 112, transportation 114, and usage 116. In certain embodiments, one or more of the foregoing stages may be eliminated; two or more stages may be consolidated; and/or one or more additional stages may be added.

The starting solution creation stage 102 may include production of one or more starting solutions or precursors thereof. The starting solution supply stage 104 may include mixing and/or diluting starting solution precursors, and supplying the resulting one or more starting solutions to the electrochemical processing stage 106. The waste processing stage 108 may include neutralizing a basic catholyte stream produced by the electrochemical processing stage 106. The stabilization stage 110 may include elevating pH of an acidic anolyte stream produced by the electrochemical processing stage 106. The output/storage stage 112 may include venting, storing, and/or and packaging a stabilized mixed oxidant solution. The transportation stage 114 may include transporting stabilized mixed oxidant solution to a point of use. The usage stage 116 may include applying the stabilized mixed oxidant solution to a fluid system (e.g., water distribution and/or recirculation system at the point of use).

In certain embodiments, production of stabilized mixed oxidant solution may be conducted in a minimally conditioned or unconditioned environment temperature (approximately 75° F., +/−25° F.). In other embodiments, one or more stages (e.g., electrochemical processing 106, stabilization 110, output/storage 112, transportation 114, and/or usage may be performed in an air-conditioned or otherwise chilled environment.

Within a flow-through electrochemical module, it is believed that a two-step oxidation process is performed. For example, if a NaCl (salt brine) solution is injected into a flow-through electrochemical module, the chloride ions are believed to undergo an initial oxidation step (e.g., to form hypochlorous acid and/or sodium hypochlorite), and the molecule(s) resulting from the initial oxidation step are believed to be further oxidized to generate the final molecule(s) of interest. Thus, if the starting solution includes hypochlorous acid and/or sodium hypochlorite in addition to or instead of salt brine, then the concentration of the final molecule(s) of interest may be enhanced.

Traditional methods for identifying and/or quantifying the specific oxidants contained in the stabilized mixed oxidant solutions produced according to methods disclosed herein have not been successful, due at least in part to the fact that chlorine is a strong oxidant and interferes with measurement. With respect to the two streams produced by flow-through electrochemical modules as disclosed herein, the anolyte stream is believed to include two or more of the following: $HOCl$, $ClO_2$, $O_3$, $Cl_2$, $O_2$, $OH^0$, and/or $OH^*$ (as may be supplemented with hydroxide (e.g., NaOH) upon execution of the stabilization step), and the catholyte stream is believed to include two or more of the following: $NaOCl$, $NaOH$, $H_2$, and $H_2O_2$.

The starting solution creation stage 102 involves the creation of a solution comprising at least one of salt brine, hypochlorous acid, and sodium hypochlorite. If the starting solution comprises salt brine, such brine may be created by mixing water and any suitable one or more type of salt, resulting in dissolution of salt in water. In one embodiment, such salt may consist of or include 99.9% pure food high grade Morton® brand sodium chloride (NaCl). In other embodiments, various other types, brands, and grades of salt may be substitute. In certain embodiments, sodium chloride may be replaced or supplemented with one or more of sodium bromide, potassium chloride, potassium iodide, and calcium chloride. Substituting calcium chloride ($CaCl_2$) for some or all sodium chloride (NaCl) may be beneficial in certain embodiments, since the solubilized calcium ion is doubly charged in comparison to a singly charged sodium ion.

In certain embodiments, water used to make salt brine may include municipal tap water; in other embodiments, highly mineralized, low mineralized, chlorinated, and/or chloraminated water may be used. In certain embodiments, conductivity of a salt brine solution may be in a range of from 5-50 millisiemens as measured with a conductivity meter. In certain embodiments, salt brine solution may be subject to one or more filtering steps after creation (e.g., by flowing brine through a screen, sand bed, a diffusion bed, and/or other filtration media.) Further details regarding creation of salt brine solutions are provided in U.S. Pat. No. 8,366,939.

In certain embodiments, a starting solution may include at least one of hypochlorous acid and sodium hypochlorite, in combination with water and/or salt brine. Various methods for producing hypochlorous acid and sodium hypochlorite are known to those skilled in the art. In certain embodiments, hypochlorous acid and/or sodium hypochlorite may be manufactured at the same facility and/or in a substantially continuous process (i.e., without requiring intervening storage and/or transportation) for feeding such composition(s) to the electrochemical processing stage 106. In other embodiments, hypochlorous acid and/or sodium hypochlorite may be produced in a different facility and/or in a substantially discontinuous process relative to the electrochemical processing stage 106, whereby hypochlorous acid and/or sodium hypochlorite may be shipped to and/or stored in a facility prior to feeding of such composition(s) to the electrochemical processing stage 106.

The starting solution supply stage 104 may include blending and/or dilution of starting solution constituents. In certain embodiments, the starting solution creation stage 102 may include creation of a concentrated precursor solution that is subject to dilution with water and/or salt brine. In certain embodiments, hypochlorous acid and/or sodium hypochlorite may be blended with water and/or salt brine to form a starting solution. In certain embodiments, pH of a starting solution may be adjusted (e.g., raised or lowered) by addition of at least one acid or base. A suitable acid for addition to a starting solution may include HCl, and a suitable base for addition to a starting solution may include NaOH. Blending and/or dilution of constituents of a starting solution may be controlled responsive to one or more sensors, such as a pH sensor, a conductivity sensor, and/or one or more sensors arranged to sense chlorine content.

In certain embodiments, starting solution may be created and fed to the flow-through electrochemical processing stage 106 in a substantially continuous process (e.g., with minimal or no intervening storage). In other embodiments, one or more storage tanks may be arranged upstream of the electrochemical processing stage 106 in order to store starting solution.

The starting solution supply stage 104 preferably includes pressurization of starting solution, such as with at least one pump or other suitable apparatus. In the electrochemical processing stage 106, the oxidation and/or reduction reactions may include production of gaseous by-products (e.g., such as hydrogen gas, oxygen gas, chlorine gas, and/or by-products of other oxidized species). Under low pressure conditions, these gaseous molecules may appear as bubbles that might interfere with fluid flow through gas flow passages and/or contact one or more electrodes within a flow-through electrochemical processing apparatus and therefore interfere with electron flow and redox reactions. In certain embodiments, the starting solution is pressurized to a level exceeding the partial pressure of at least one gas (and more preferably exceeding partial pressure of all gases) subject to being created in a flow-through electrochemical processing apparatus and associated downstream components, thereby inhibiting formation of bubbles. Partial pressure preferably exceeds at least one of hydrogen gas, oxygen gas, chlorine gas within a flow-through electrochemical processing apparatus as described herein. Pressure within a flow-through electrochemical processing apparatus may also be adjusted (e.g., using a pressure regulator or other pressure adjusting element(s)) to an appropriate level to adjust reaction kinetics within the apparatus. A bypass line may optionally be used to help adjust pressure before starting solution reaches a pressure regulator.

In certain embodiments, temperature of starting solution may be adjusted in the starting solution supply stage 104 and/or in the electrochemical processing stage 106 in order to enhance reaction kinetics. For example, temperature of starting solution and/or temperature within the flow-through electrochemical processing apparatus may be adjusted (e.g., increased) in order to enhance the likelihood of a particular oxidation reaction, and increase the concentration of one or more desired molecules of interest.

In the electrochemical processing stage 106, at least one starting solution is flowed through an electrochemical module including a first passage and a second passage separated by an ion permeable membrane while electric power is applied between (i) an anode in electrical communication with the first passage and (ii) a cathode in electrical communication with the second passage. In certain embodiments, composition and concentration of starting solution flowing through the first passage and the second passage may be substantially the same (e.g., with a first portion of a starting solution passing through the first passage, and a second portion of the starting solution passing through the first passage (wherein flow rate may be substantially the same or may be substantially different between the first passage and the second passage)). In other embodiments, at least one parameter of composition and concentration of starting solution may differ between the first passage and the second passage (e.g., with a first starting solution passing through the first passage, and with a second starting solution passing through the second passage), wherein flow rate may be substantially the same or may be substantially different between the first passage and the second passage. In certain embodiments, flow of starting solution through the anode chamber is slower than flow rate through the cathode chamber, to permit longer residence time of starting solution (electrolyte) in the anode chamber and permit an increased number of oxidation reactions.

In certain embodiments, multiple flow-through electrochemical modules as described herein may be operated fluidically in parallel.

In certain embodiments, multiple flow-through electrochemical modules as described herein may be operated fluidically in series, with anolyte solution generated by a first module being used as a starting solution for at least the anode chamber of at least one downstream module, in order to promote an increased number of oxidation reactions.

In still further embodiments, multiple flow-through electrochemical modules as described herein may be operated fluidically in series-parallel. For example, one group of two or more modules may be arranged fluidically in series, and multiple series groups may further be arranged fluidically in parallel.

A simplified schematic cross-sectional view of a flow-through electrochemical module 225 is shown in FIG. 2. The module includes a first flow-through chamber 236 comprising an anode 230, a second flow-through chamber 238 comprising a cathode 234, and a membrane (e.g., an ion-permeable membrane) 232 arranged between the first chamber 236 and the second chamber 238. The anode 230 and cathode 234 are in electrical communication with terminals 215A, 215B, respectively. In operation, a first starting solution or first starting solution portion is supplied to the first chamber 236 through a first chamber inlet port 221A, and a second starting solution or second starting solution portion is supplied to the second chamber 234 through a second chamber inlet port 223A. Electric power is supplied across the anode 230 and cathode 234 to electrolyze the contents of the first chamber 236 and the second chamber 238 to yield an anolyte solution that exits the first chamber 236 through a first chamber outlet port 221B, and to yield a catholyte solution that exits the second chamber 238 through a second chamber outlet port 223B.

In certain embodiments, an anode 230 may be formed of titanium coated with a material comprising iridium, rubidium, ruthenium, and tin. In one embodiment, the coating material includes iridium content of 48%-24%, tin content of 40%-54%, ruthenium content of 8%-15%, and rubidium content of 4%-7%. In other embodiments, the anode comprises a coating of platinum and iridium. The composition of the anode may be varied based on conductivity, durability, and cost considerations. In certain embodiments, coating materials provided by Siemens may be used.

In certain embodiments, a membrane 232 may comprise a ceramic material (e.g., including but not limited to glass bonded ceramic materials). In certain embodiments, the membrane 232 may comprise alumina. In other embodiments, the membrane may comprise a blend of alumina and zirconia materials. Various materials can also be used for the membrane 232 depending on considerations such as porosity, insulation characteristics, durability, and cost.

In certain embodiments, a cathode 234 may comprise titanium. In other embodiments, a cathode 234 may comprise different materials. The composition of the cathode may be varied based on conductivity, durability, and cost considerations.

Geometry and dimensions of the anode 230, cathode 234, membrane 232, and chambers 236, 238 may be varied in order to provide desired performance characteristics. In certain embodiments, anode, membrane, and cathode elements may be arranged as generally flat plates. In other embodiments, anode, membrane, and cathode elements may be arranged concentrically in a generally cylindrical apparatus (e.g., such as reactor cells made available by the VIIIMT Institute in Moscow, Russia.) In certain embodiments, length of flow-through chambers may be adjusted (e.g., lengthened) and/or fluid flow rate may be adjusted (e.g., reduced) to increase residence time of starting solution in the chambers to increase the likelihood of contact of ions in solution with electrode (anode or cathode) surfaces for oxidation either once, twice, or three or more times. Anode and cathode surface areas may also be adjusted by altering geometry, size, and/or surface characteristics (e.g., texturing) in order to enhance likelihood of oxidation of ions either once, twice, or three or more times.

In certain embodiments, power supply components and/or electrode materials may be adjusted to allow increased power to be supplied to a flow-through electrochemical module. In an electrochemical cell, the number of oxidizing events will be related to the voltage applied (to overcome the electrochemical potential of a given molecule or atom) and the amperage through the cell (more electrons are able to flow through the cell and perform redox reactions). A given oxidation/reduction reaction will be based on both the number of interactions between solubilized molecules/atoms with a given electrode surface and the availability of electrons from the power supply (amperage).

An exemplary flow-through electrochemical module 325 is illustrated in FIG. 4. The module 325 includes a center anode 330. A membrane 332 (e.g., ceramic membrane) having an annular shape surrounds the anode 330. Beyond the membrane 332, and forming an exterior portion of the electrochemical module 325, is the exterior cathode 334. The length of the center anode 330 may be greater than the exterior cathode 334, and the membrane 332 may also be also longer than the exterior cathode 334. A first (inside) passage 336 is arranged between the center anode 330 and the membrane 332. A second (outside) outside passage 338 is arranged between the membrane 332 and the exterior cathode 334.

At the ends of the module 325 are inside collectors 322A, 322B and outside collectors 324A, 324B, such as may be formed of polytetrafluoroethylene material or another fluoropolymer material, or may be formed of polyethylene with addition of antioxidant materials. The upstream inside collector 322A receives starting solution from an inlet port 321A and leads into the first (inside) passage 336 that supplies anolyte solution to the downstream inside collector 322B and outlet port 321B. In a corresponding manner, the upstream outside collector 324A receives starting solution from an inlet port 323A and leads into the second (outside) passage 338 that supplies catholyte solution to the downstream outside collector 324B and outlet port 323B. In one embodiment, each port 321A, 321B, 323A, 323B may have female ⅛ inch national pipe thread fittings; in other embodiments, other sizes and/or types of fittings may be used—including, but not limited to, hose barb fittings.

FIG. 3 is a schematic diagram showing arrangement of a mixed oxidant solution production system 300 including multiple flow-through electrochemical modules 325A-325B (each according to the module 325 illustrated in FIG. 4) and associated components. (The system 300 may be operated to perform the stages of electrochemical processing 106, waste processing 108, and stabilization 110 as depicted in FIG. 1). At least one starting solution source 301 (which may include a pressure regulator (not shown)) supplies starting solution through at least one feed valve 302 arranged to supply one or more starting solutions to starting solution supply headers 307, 309 and inlet pipes 311, 313A. A first inlet pipe 311 is arranged to supply starting solution to a flow-through anode chamber 336, and a second inlet pipe is arranged to supply starting solution to a flow-through cathode chamber 338, wherein the anode chamber and cathode chamber are separated by a membrane 332. A power supply 308 is arranged to supply electrical direct current (DC) via terminals 315, 316 arranged to apply voltage between an anode in electrical communication with the anode chamber 336 and a cathode in electrical communication with the cathode chamber 338, to electrolyze starting solution present in the flow-through electrochemical module 325. Catholyte solution generated by the cathode chamber 338 flows to an outlet pipe 313B, catholyte header 319, and needle valve 360 for subsequent neutralization (i.e., by reducing pH). Anolyte solution generated by the anode chamber 336 flows to an outlet pipe 311B, anolyte header 317, and three-way valve 340 for subsequent stabilization (i.e., by increasing pH). Catholyte solution generated by each module 325 has a basic pH (e.g., typically a pH value in a range of from 9 to 12), and anolyte solution generated by each module has an acidic pH (e.g., typically a pH value in a range of from 1 to 4).

In one embodiment, ten groups of four flow-through electrochemical modules 325 (such as illustrated in FIG. 4) may be employed, for a total of forty flow-through electrochemical modules. Each reactor cell 325 may receive 12 volts and 10 amps. Within each group, two of the four modules 325 may be wired electrically in parallel, with the two modules of each group being wired in series with another two modules in the group of four. FIG. 3 illustrates only two modules 325A-325B. In other embodiments different wiring configurations are employed, including all reactor modules 325 being operated electrically in series or in parallel.

A large number of modules 325 form a module bank that allows for the production of large quantities of mixed oxidant solution. With this number of modules 325, in one embodiment the pressure and aggregate flow rate of starting solution entering the modules may be adjusted to 5-10 psi and 1-2 gal/minute. The number of modules used can be increased or decreased to meet production needs, and the pressure and/or flow rate of starting solution supplied to the module bank may be varied depending on factors including the number, size, and configuration of modules 325, the characteristics of the at least one starting solution, and the desired characteristics of the resulting anolyte solution.

The power supply 308 may comprise a linear unregulated unit (e.g., produced by Allen-Bradley), a linear regulated power supply, or an AC/DC/AC/DC switching power supply. Multiple power supplies 308 can also be employed. The electric power to each module 325 from the power supply 308 can also be varied as needed.

Continuing to refer to FIG. 3, the catholyte stream received from the outlet pipe 313B, catholyte header 319, and needle valve 360 flows past a pH meter 361, a three-way valve 362, and a flow sensor 364 to reach a waste neutralization element 365 arranged to receive a flow of acid from an acid source 366 and an acid flow control valve 368. Various types of acid may be used, including but not limited to hydrochloric acid. Acid may be supplied to the neutralization element 365 (which may include a mixer, such as a flow-through mixer) responsive to signals from the pH meter 361 and flow sensor 364 to neutralize or at least partially neutralize the catholyte (e.g., preferably to a pH value in a range of from 7 to 9, or more preferably in a range of from 7 to 8) to permit disposal of the neutralized catholyte product (e.g., by directing such product to a sewer).

The anolyte stream received from the outlet pipe 311B, anolyte header 317, and three-way valve 340 flows past a pH meter 341 then through a needle valve 342, a stabilization (e.g., base addition) element 344, a mixer 349, another pH meter 351, and a flow meter 354 before flowing to an output stage 500. The stabilization element 344 is arranged to receive a flow of base (preferably one or more hydroxides, such as but not limited to sodium hydroxide, potassium hydroxide, and the like) from a base (e.g., hydroxide) source 346 and a base flow control valve 348. Base (e.g., hydroxide) may be supplied to the stabilization element 344 responsive to signals from one or both pH meters 341, 351 and a flow sensor (not shown) to elevate pH of the anolyte from a starting acidic value (e.g., in a pH range of from 2 to about 4) to an elevated pH value in the basic range, (preferably a pH value of at least about 9.0, at least about 9.5, at least about 10.0, at least about 10.5, at least about 11.0, at least about 11.5, at least about 12.0, at least about 12.5, or at least about 13.0)—to yield the mixed oxidant solution.

The pH stabilization step is preferably performed a very short distance downstream of the flow-through electrochemical modules 325 to permit such stabilization to be performed immediately after anolyte production—thereby suppressing chlorine gas and minimizing degradation of mixed oxidants in the anolyte solution. Preferably, pH stabilization is performed on anolyte solution within less than about 5 seconds (more preferably within less than about 3 seconds) after anolyte exits the flow-through electrochemical modules 325.

FIG. 9 is a line chart depicting total chlorine (ppm) versus time (days) for mixed oxidant solutions produced using the system of FIG. 3. As shown in FIG. 9, chlorine content of an initially acidic anolyte solution having pH adjusted (e.g., with addition of sodium hydroxide) to a value of 7.73 degraded rapidly, from an initial chlorine value exceeding 4500 ppm to a value of approximately 1300 within 8 days. Increasing the pH of anolyte solutions resulted in enhanced stability, as shown in the data generated for pH-modified anolyte solutions having pH values of 9.1, 10.04, 11.05, and 12.09, respectively. At a pH value of 10.04, total chlorine content of a pH-modified anolyte solution diminished by less than about 10% (from a starting value of approximately 4700 ppm) after 28 days. At a pH value of 11.05, total chlorine content of a pH-modified anolyte solution diminished by less than about 5% or less (from a starting value of approximately 4900 ppm) after 28 days At a pH value of 12.09, total chlorine content of a pH-modified anolyte solution was substantially unchanged after 28 days at a value of approximately 5000 ppm. FIG. 9 therefore shows that modifying pH of initially acidic anolyte to elevated pH (e.g., at least about 9.0, at least about 10.0, at least about 11.0, at least about 12.0, or another intermediate value or value exceeding 12.0) beneficially improves stability of chlorine species in mixed oxidant solutions.

Referring back to FIG. 3, various elements of the system 300 may be automated and controlled via a controller 390. The flow-through electrochemical modules 325 may be periodically cleaned by suspending production of mixed oxidant solution, and circulating one or more solutions through the modules via recirculation lines 368, 369 and recirculation element 370. In certain embodiments, cleaning may involve three cycles: (a) an initial rinse cycle, (b) an acid rinse cycle, and (c) a final rinse cycle. Cleaning may be performed according to any suitable schedule, such as hourly, once every few hours, once per day, or any other suitable interval. Increased frequency of cleaning cycles is expected to enhance quality of the resulting mixed oxidant solution. An initial rinse cycle may last approximately 80 seconds, followed by an acid rinse cycle (e.g., using 0.1 to 5% hydrochloric acid (HCl)) that may last for approximately five minutes, followed by circulation of starting solution for approximately 160 seconds before the power supply 308 is reactivated for continued production of stabilized mixed oxidant solution. Timing and duration of cleaning cycles may depend on factors such as module size, flow rates, cleaning frequency, cleaning solution concentration, and desired results.

FIG. 5 is a schematic diagram showing components of an output subsystem 500 arranged to receive a stabilized mixed oxidant solution from the production system 300 of FIG. 3. After passage through the pH sensor 351 and flow sensor 354, the solution may flow past a vent line 502 to vent any gas produced during the process. The stabilized mixed oxidant solution 350 then enters a holding tank 510, where it may be monitored for quality (e.g., to confirm that the pH value desirably is at least about 9.0, at least about 9.5, at least about 10.0, at least about 10.5, at least about 11.0, at least about 11.5, at least about 12.0, at least about 12.5, or at least about 13.0.) Titration may also be conducted (e.g., using a Hach digital titrator Method 8209 (Hach Co., Loveland, Colo.)) to measure the total chlorine content, to preferably yield a total chlorine value of preferably at least about 1000 ppm, or preferably at least about 2000 ppm, or preferably at least about 3000 ppm, or preferably at least about 4000 ppm, or preferably at least about 5000 ppm. In certain embodiments, the total chlorine value of the stabilized mixed oxidant solution may desirably be in a range of from about 1000 ppm to about 3500 ppm.

In certain embodiments, the stabilized mixed oxidant solution 350 may be pumped (using pump 515) to an insulated storage tank 520, wherein insulation 522 helps keep the temperature of the solution 350 consistent. A desired temperature for the solution is in a range of from 50° F.-80° F. Degradation of the mixed oxidant solution 350 depends on temperature and time, with degradation being more rapid at high temperatures (and particularly in direct sunlight). Reducing solution temperature may enhance shelf life. The anolyte solution exiting the flow-through electrochemical modules may have a temperature of approximately 100° F. Chilling the mixed oxidant solution immediately after stabilization is believed to permit further enhanced shelf life. The storage tank 520 may optionally be refrigerated, such as by using a fluoroplastic heat exchanger constructed utilizing polyvinylidene fluoride and/or polytetrafluoroethylene materials.

From the storage tank 520, the stabilized mixed oxidant solution may be pumped (using pump 525) into suitable (e.g., polyethylene) containers 530 such as totes or barrels. The stabilized mixed oxidant solution is a dilute oxidizer and can be corrosive over time. Suitable best materials for packaging and handling these solutions include fluoroplastics, PVC, and polyethylene.

Following packaging, the stabilized mixed oxidant solution 350 is ready for the transportation 540 to a customer/point of use 550. A customer may supply (e.g., inject) the stabilized mixed oxidant solution into suitable conduits or containers at a point of use, such as (but not limited to) a water treatment, water distribution, and/or water recirculation system. The customer 550 is able to utilize the stabilized mixed oxidant solution without requiring on-site generation of mixed oxidant solution with attendant difficulties of maintenance and quality control. Moreover, due to the extended shelf life of the stabilized mixed oxidant solution, the customer has increased flexibility to store mixed oxidant solution at the customer site with reduced concern regarding waste or disposal of unused "expired" product.

The stabilized mixed oxidant solution may beneficially reduce, remove, or prevent formation of deposits in such systems. Such solution prevents nucleation, which is a key requirement for the crystallization of minerals from solution directly on surfaces. Nucleation is the beginning of scales, films and other deposits. Existing mineral scales cannot be sustained and new scales cannot form without continuous nucleation. The stabilized mixed oxidant solution disrupts the attachment mechanisms of mineral scales and other deposit constituents in water systems, and results in improved water quality that is maintained with usage of the product. Water treated with the stabilized mixed oxidant solution may be used to eliminate scale and other deposition in the entire water distribution system without interruption to facility operation, thereby preventing the need for facility shutdown for hazardous acid treatment or pipe removal and replacement. Deposition removal may be effective in water systems, equipment, floors, walls, and drains, whereby metal and plastic surfaces may become exceptionally clean at the microscopic as well as the visual level. By removing and preventing the formation of scales and biofilm in pipe, chlorine demand is reduced so that residuals can be maintained thereby elevating water quality.

As indicated previously, numerous uses exist for stabilized mixed oxidant solutions produced according to the present invention. Exemplary water distribution and water recirculation systems utilizing such solutions are illustrated in FIGS. 6-8. As noted previously, stabilized mixed oxidant compositions described herein may be used to provide scale control utility as well as primary disinfection or secondary disinfection utility (depending on concentration). Although the systems described in connection with FIGS. 6-8 are directed primarily to usage of stabilized mixed oxidant compositions as a secondary disinfectant/scale control additive, it is to be appreciated that stabilized mixed oxidant compositions disclosed herein may be also utilized for primary disinfection utilizing conventional disinfectant addition equipment.

FIG. 6 is a schematic diagram showing components of a first water distribution system 600 arranged to receive a mixed oxidant solution according to the present invention. A water source 610 may be arranged to supply water to at least one water distribution element 650 arranged to supply water to multiple downstream points of use 651A-651X. A primary disinfection unit 620, a flow sensor 631, a secondary treatment unit 640, and at least one water property sensor 633 (e.g., pH sensor, total chlorine sensor, and/or other type of sensor(s)) may be arranged between the water source 610 and the distribution element 650. The secondary treatment unit 640 is arranged to receive stabilized mixed oxidant solution from a reservoir or container 642 and a pump 644 following passage through a flow sensor 646. A controller 690 may be arranged to control the supply of stabilized mixed oxidant solution to the secondary treatment unit 640 responsive to the flow sensor(s) 631, 646 and the at least one water property sensor 633. The primary disinfection unit 620 may be arranged to supply chlorine gas, liquid bleach (hypochlorite), hydrogen peroxide, and/or other chemicals to water received from the water source 610. In one embodiment, the secondary treatment unit 640 is arranged within the same facility 681 as the at least one distribution element 650. In another embodiment, both the primary disinfection unit 620 and the secondary treatment unit are arranged within a single facility 680. In certain embodiments, the primary disinfection unit 620 may be omitted. In other embodiments, the primary disinfection unit 620 may be configured to supply stabilized mixed oxidant composition, and the secondary treatment unit 640 may be omitted.

In certain embodiments, compositions used for primary disinfection and secondary treatment may be added to water in a single treatment unit. In certain embodiments, compositions used for primary disinfection and secondary treatment may be blended with one another prior to addition to water. In one embodiment, a stabilized mixed oxidant solution may be co-injected and/or blended with at least one of liquid bleach (hypochlorite) and hydrogen peroxide for addition to a water distribution or water recirculation system.

FIG. 7 is a schematic diagram showing components of a second water distribution system 700 arranged to receive a mixed oxidant solution according to the present invention, wherein a stabilized mixed oxidant solution may be co-injected and/or blended with a primary disinfectant for addition to water upstream of a water distribution element 750. A water source 710 may be arranged to supply water to at least one water distribution element 750 arranged to supply water to multiple downstream points of use 751A-751X. A flow sensor 731, a single treatment unit 730, and at least one water property sensor 733 (e.g., pH sensor, total chlorine sensor, and/or other type of sensor(s)) may be arranged between the water source 710 and the distribution element 750. The single treatment unit 730 is arranged to receive primary disinfectant from a first reservoir or container 722 and a first pump 724 following passage through a first flow sensor 726, and is further arranged to receive stabilized mixed oxidant solution from a second reservoir or container 742 and a second pump 744 following passage through a second flow sensor 746. The primary disinfectant and the stabilized mixed oxidant solution may be blended prior to, or co-injected into, the treatment unit 730 (which preferably includes a flow-through mixer). A controller 790 may be arranged to control the supply of primary disinfectant and stabilized mixed oxidant solution to the single treatment unit 730 responsive to the flow sensor(s) 731, 726, 746 and the at least one water property sensor 733.

FIG. 8 is a schematic diagram showing components of a water recirculation system 800 arranged to receive a mixed oxidant solution according to the present invention. A water source 811 (e.g., tank or reservoir) may be arranged to supply water to at least one point of use 860. A primary disinfection unit 820, a flow sensor 831, a secondary treatment unit 840, and least one water property sensor 833 (e.g., pH sensor, total chlorine sensor, and/or other type of sensor(s)), and a pump 859 may be arranged between the water source 811 and the point of use 860. (In certain embodiments, the primary disinfection unit 820 may be omitted, while in other embodiments, the primary disinfection unit 820 may be configured to supply stabilized mixed oxidant composition, and the secondary treatment unit 840 may be omitted.) The secondary treatment unit 840 is arranged to receive stabilized mixed oxidant solution from a reservoir or container 842 and a pump 844 following passage through a flow sensor 846. A controller 890 may be arranged to control the supply of stabilized mixed oxidant solution to the secondary treatment unit 840 responsive to the flow sensor(s) 831, 846 and the at least one water property sensor 833. A recirculation line 865 may be arranged to recirculate at least a portion of the water from the point of use 860 to the water source 811. A make-up source 810 may be arranged to supply additional water to the water source 811 as needed. In certain embodiments, the point of use may include an aquaculture system, a hydroponic food production system, a swimming pool, a cooling water system, or another agricultural or industrial water recirculation system.

FIG. 10 is a table summarizing characteristics including total chlorine, pH, oxidation-reduction potential (ORP), conductivity, sodium ion concentration, chlorine ion concentration, and sodium/chloride ion ratio for the following five products: (1) 12.5% hypochlorite bleach, (2) 6% hypochlorite bleach, (3) Clearitas® mixed oxidant solution, (4) Miox™ mixed oxidant solution, and (5) a (new) stabilized mixed oxidant solution according to the present invention. Various differences between the five compositions are apparent.

Relative to Applicants' stabilized mixed oxidant solution, both hypochlorite (liquid bleach) compositions have extremely high total chlorine (e.g., 37 to 90 times higher than Applicant's stabilized mixed oxidant solution), high pH, high conductivity (e.g., 7.5 times higher than Applicant's stabilized mixed oxidant solution), but lower ORP and lower ratio of sodium/chloride ion ratio. It is understood that hypochlorite (bleach) does not contain a significant number of mixed oxidants. Applicants have observed that hypochlorite (liquid bleach) has very limited ability to control deposits composed of both organic and inorganic constituents in drinking water systems, in comparison to the high efficacy in controlling deposits characteristic of Applicant's stabilized mixed oxidant solution.

Clearitas® mixed oxidant solution (previously sold as RE-Ox® scale control additive) has been commercialized by the assignee of the present invention for a period of multiple years. Such solution may be produced substantially in accordance with the method described in U.S. Pat. No. 8,366,939. Relative to Applicants' stabilized mixed oxidant solution, Clearitas® solution has significantly lower total chlorine (about 600 ppm versus 1550 ppm for the Applicants' stabilized mixed oxidant solution), substantially lower conductivity, and substantially lower pH (i.e., 7.86 versus 17.4), but increased ORP and increased ratio of sodium/chloride ion ratio. Tests performed by the assignee of the present application confirm that a lower concentration of Applicants' stabilized mixed oxidant solution provides comparable scale control benefits to the use of Clearitas® solution at higher concentration, with Applicant's stabilized mixed oxidant solution further exhibiting significantly increased effective shelf life (e.g., on the order of at least 2-5 times greater than Clearitas® solution).

Miox™ mixed oxidant solution is typically generated at a point of use through operation of an on-site mixed oxidant production apparatus commercially available from Miox Corporation (Albuquerque, N. Mex., USA). A two-month old refrigerated sample of a mixed oxidant solution produced by a Miox mixed oxidant production apparatus (believed to have utilized a production method according to at least one of U.S. Pat. No. 5,316,740 and U.S. Pat. No. 7,922,890) was analyzed as the basis for comparison. Relative to Applicants' stabilized mixed oxidant solution, the Miox™ mixed oxidant solution has higher total chlorine (about 3780 versus 1550 ppm for Applicants' stabilized mixed oxidant solution), lower pH (about 9.12 versus about 10.46), higher ORP, higher conductivity, and similar sodium/chloride ion ratio. Effectiveness of the Miox™ mixed oxidant solution in performing scale control was not evaluated.

Novel systems and methods for producing and using mixed oxidant solutions exhibiting enhanced effectiveness and enhanced stability compared to prior solutions have been disclosed herein, with particular utility for water treatment (e.g., primary disinfection or secondary disinfection) and/or reducing deposits in water distribution or water recirculation systems.

Embodiments as disclosed herein may provide beneficial technical effects including provision of primary disinfection treatment or secondary disinfection treatment and scale control compositions suitable for water distribution systems with enhanced effectiveness (thereby reducing shipping weight, reducing storage volume, and reducing size and cost of dosing equipment) in combination with extended effective shelf life; reducing chlorine demand and chlorine disinfection by-products; providing enhanced scale control and removal; and providing water softening utility, while avoiding use of hazardous chemicals.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Various combinations and sub-combinations of the structures described herein are contemplated and will be apparent to a skilled person having knowledge of this disclosure. Any of the various features and elements as disclosed herein may be combined with one or more other disclosed features and elements unless indicated to the contrary herein. Correspondingly, the invention as hereinafter claimed is intended to be broadly construed and interpreted, as including all such variations, modifications and alternative embodiments, within its scope and including equivalents of the claims.

What is claimed is:

1. A method for producing a mixed oxidant solution comprising a plurality of different oxidants, the method comprising:

flowing at least one starting solution through at least one flow-through electrochemical module comprising a first passage and a second passage separated by an ion permeable membrane while electric power is applied between (i) an anode in electrical communication with the first passage and (ii) a cathode in electrical communication with the second passage, wherein a first solution or first portion of the at least one starting solution is flowed through the first passage to form an anolyte solution having an acidic pH, and a second solution or second portion of the at least one starting solution is simultaneously flowed through the second passage to form a catholyte solution having a basic pH; and contacting the anolyte solution with a hydroxide solution to attain a pH value of at least about 9.0 to yield said mixed oxidant solution;

wherein the at least one starting solution comprises at least one of salt brine, hypochlorous acid, and sodium hypochlorite.

2. A method according to claim 1, further comprising discarding the catholyte solution.

3. A method according to claim 1, wherein characteristics of the at least one starting solution, flow rate of the at least one starting solution, materials of construction of the at least one flow-through electrochemical module, dimensions of the at least one flow-through electrochemical module, number of the at least one flow-through electrochemical module, conformation of the at least one flow-through electrochemical module, and field density of the applied electric power are selected to yield a mixed oxidant solution comprising a plurality of different oxidants that comprises a total chlorine value of at least about 3,000 ppm.

4. A method according to claim 1, wherein characteristics of the at least one starting solution, flow rate of the at least one starting solution, materials of construction of the at least one flow-through electrochemical module, dimensions of the at least one flow-through electrochemical module, number of the at least one flow-through electrochemical module, conformation of the at least one flow-through electrochemical module, and field density of the applied electric power are selected to yield a mixed oxidant solution comprising a plurality of different oxidants that comprises an oxidation-reduction potential (ORP) value in a range of from 600 mV to 800 mV.

5. A method according to claim 1, wherein characteristics of the at least one starting solution, flow rate of the at least one starting solution, materials of construction of the at least one flow-through electrochemical module, dimensions of the at least one flow-through electrochemical module, number of the at least one flow-through electrochemical module, conformation of the at least one flow-through electrochemical module, and field density of the applied electric power are selected to yield a mixed oxidant solution comprising a plurality of different oxidants that comprises a ratio of Na+ (in g/L according to Method EPA 300.0) to Cl− (in g/L according to Method EPA 6010) of at least about 1.5.

6. A method according to claim 1, further comprising packaging the mixed oxidant solution in at least one container, and transporting said at least one container to a treatment facility associated with said water distribution or water recirculation system.

7. A method according to claim 1, wherein within the at least one flow-through electrochemical module the anode is centrally arranged, the membrane surrounds the anode, the cathode surrounds the membrane, the first passage comprises an inner passage arranged between the anode and the membrane, and the second passage comprises an outer passage arranged between the membrane and the cathode.

8. A mixed oxidant solution comprising a plurality of different oxidants produced by a method comprising:
flowing at least one starting solution through at least one flow-through electrochemical module comprising a first passage and a second passage separated by an ion permeable membrane while electric power is applied between (i) an anode in electrical communication with the first passage and (ii) a cathode in electrical communication with the second passage, wherein a first solution or first portion of the at least one starting solution is flowed through the first passage to form an anolyte solution having an acidic pH, and a second solution or second portion of the at least one starting solution is simultaneously flowed through the second passage to form a catholyte solution having a basic pH; and
contacting the anolyte solution with a hydroxide solution to attain a pH value of at least about 9.0 to yield said mixed oxidant solution;
wherein the at least one starting solution comprises at least one of salt brine, hypochlorous acid, and sodium hypochlorite.

9. A mixed oxidant solution according to claim 8, wherein the at least one starting solution comprises salt brine.

10. A mixed oxidant solution according to claim 8, wherein the at least one starting solution comprises at least one of hypochlorous acid and sodium hypochlorite.

11. A mixed oxidant solution according to claim 8, wherein said contacting the anolyte solution with a hydroxide solution attains a pH value of at least about 10.5.

12. A mixed oxidant solution according to claim 8, wherein said contacting the anolyte solution with a hydroxide solution attains a pH value of at least about 12.0.

13. A mixed oxidant solution comprising a plurality of different oxidants according to claim 8, wherein the solution comprises a total chlorine value of at least about 3,000 ppm.

14. A mixed oxidant solution comprising a plurality of different oxidants according to claim 8, wherein the solution comprises an oxidation-reduction potential (ORP) value in a range of from 600 mV to 800 mV.

15. A mixed oxidant solution comprising a plurality of different oxidants according to claim 8, wherein the solution comprises a ratio of Na+ (in g/L according to Method EPA 300.0) to Cl− (in g/L according to Method EPA 6010) of at least about 1.5.

16. A blended liquid product comprising the mixed oxidant solution of claim 8 and a primary disinfectant composition.

17. The blended liquid product of claim 16, wherein the primary disinfectant comprises at least one of hypochlorite and hydrogen peroxide.

18. A method for promoting disinfection and reduction of deposits in a water distribution or water recirculation system with a mixed oxidant solution comprising a plurality of different oxidants produced by flowing at least one starting solution through at least one flow-through electrochemical module comprising a first passage and a second passage separated by an ion permeable membrane while electric power is applied between (i) an anode in electrical communication with the first passage and (ii) a cathode in electrical communication with the second passage, wherein a first solution or first portion of the at least one starting solution is flowed through the first passage to form an anolyte solution having an acidic pH, and a second solution or second portion of the at least one starting solution is simultaneously flowed through the second passage to form a catholyte solution having a basic pH, and contacting the anolyte solution with a hydroxide solution to attain a pH value of at least 9.0 to yield said mixed oxidant solution, wherein the at least one starting solution comprises at least one of salt brine, hypochlorous acid, and sodium, hypochlorite, the method comprising:
supplying an effective amount of the mixed oxidant solution to the water distribution or water recirculation system.

19. A method according to claim 18, wherein the supplying of mixed oxidant solution to the water distribution or recirculation system is sufficient to elevate oxidant concentration in the water distribution or water recirculation system by 0.2 ppm to 0.6 ppm relative to water present in the water distribution or water recirculation system prior to the step of supplying mixed oxidant solution.

20. A method according to claim 19, wherein water present in the water distribution or water recirculation system is devoid of primary disinfectant prior to the step of supplying mixed oxidant solution.

21. A method according to claim 18, wherein the supplying of mixed oxidant solution to the water distribution or recirculation system is sufficient to elevate oxidant concentration in the water distribution or water recirculation system by 1 ppb to 100 ppb relative to water present in the water distribution or water recirculation system prior to the step of supplying mixed oxidant solution.

22. A method according to claim 21, wherein water present in the water distribution or water recirculation system comprises a primary disinfectant prior to the step of supplying mixed oxidant solution.

23. A method according to claim 18, wherein the water distribution or water recirculation system comprises water lines within a building.

24. A method according to claim 18, wherein the water distribution or water recirculation system comprises a water recirculation system.

25. A method according to claim 18, wherein the water distribution or water recirculation system comprises a drinking water distribution system.

26. A method according to claim 18, wherein the drinking water distribution system comprises a municipal or community drinking water distribution system arranged to supply potable water to water utilizing facilities of a plurality of different customers.

27. A method according to claim 18, wherein said supplying said mixed oxidant solution comprising a plurality of different oxidants to the water distribution or water recirculation system is performed at the same time as or after water in said water distribution or water recirculation system is disinfected with a primary disinfectant.

28. A method according to claim 18, wherein said supplying said mixed oxidant solution comprising a plurality of different oxidants to the water distribution or water recirculation system is performed at the same facility as said supplying of primary disinfectant to the water distribution or water recirculation system.

29. A method according to claim 18, wherein supplying step comprises (i) supplying said mixed oxidant solution comprising a plurality of different oxidants to the water distribution or water recirculation system during an initial treatment period at a first ratio of mixed oxidant solution comprising a plurality of different oxidants to water to be treated, followed by (ii) supplying said mixed oxidant solution comprising a plurality of different oxidants to the water distribution or water recirculation system during a subsequent maintenance period at a second ratio of mixed oxidant solution comprising a plurality of different oxidants to water to be treated, wherein the second ratio is substantially lower than the first ratio.

* * * * *